(12) United States Patent
Sullivan

(10) Patent No.: US 6,179,788 B1
(45) Date of Patent: *Jan. 30, 2001

(54) GUIDE WIRE WITH MULTIPLE RADIOPAQUE SECTIONS AND METHOD OF USE

(75) Inventor: Daniel J. Sullivan, Plymouth, MN (US)

(73) Assignee: SciMed Life Systems, Inc., Maple Grove, MN (US)

( * ) Notice: Under 35 U.S.C. 154(b), the term of this patent shall be extended for 0 days.

This patent is subject to a terminal disclaimer.

(21) Appl. No.: 08/673,674

(22) Filed: Jun. 26, 1996

Related U.S. Application Data

(63) Continuation of application No. 07/969,047, filed on Oct. 30, 1992, which is a continuation of application No. 07/452,710, filed on Dec. 19, 1989, now Pat. No. 5,209,730.

(51) Int. Cl.⁷ .................................................. A61M 29/00
(52) U.S. Cl. ........................ 600/585; 606/194; 604/96.01
(58) Field of Search .................................... 606/191, 192, 606/194, 195; 604/95–101, 101.01, 103.03, 103.04, 103.1; 128/657, 658, 772; 600/585

(56) References Cited

U.S. PATENT DOCUMENTS

| | | |
|---|---|---|
| 3,605,750 | 9/1971 | Sheridan et al. . |
| 3,847,157 | 11/1974 | Caillouette et al. . |
| 4,027,659 | 6/1977 | Slingluff . |
| 4,279,252 | 7/1981 | Martin . |
| 4,469,483 | 9/1984 | Becker et al. . |
| 4,538,622 | 9/1985 | Samson et al. . |
| 4,554,929 | 11/1985 | Samson et al. . |
| 4,577,637 | 3/1986 | Mueller, Jr. . |
| 4,641,654 | 2/1987 | Samson et al. . |
| 4,657,024 | 4/1987 | Coneys . |
| 4,671,291 | 6/1987 | Wilson . |
| 4,796,637 | 1/1989 | Mascuch et al. . |
| 4,821,722 | 4/1989 | Miller et al. . |
| 4,838,879 | 6/1989 | Tanabe et al. . |
| 4,922,924 | 5/1990 | Gambale et al . |
| 4,946,466 | 8/1990 | Pinchuk et al. . |
| 5,021,043 | 6/1991 | Becker . |
| 5,147,317 | * 9/1992 | Shank et al. .......................... 604/164 |
| 5,154,179 | 10/1992 | Ratner . |
| 5,169,386 | 12/1992 | Becker et al. . |
| 5,174,302 | 12/1992 | Palmer et al. . |
| 5,209,730 | * 5/1993 | Sullivan ................................ 604/56 |

FOREIGN PATENT DOCUMENTS

WO 86/06285 11/1986 (WO).

* cited by examiner

Primary Examiner—Michael H. Thaler
Assistant Examiner—William Lewis
(74) Attorney, Agent, or Firm—Crompton, Seager & Tufte, LLC

(57) ABSTRACT

A guide wire is disclosed which has a radiopaque distal lip and three or nor discrete highly radiopaque sections separated by relatively non-radiopaque sections. The highly radiopaque sections may be formed of coils and may have a width greater than their diameter. A method of marking the position of an intravascular anatomical feature (e.g., a stenosis) using the guide wire is also disclosed.

12 Claims, 1 Drawing Sheet

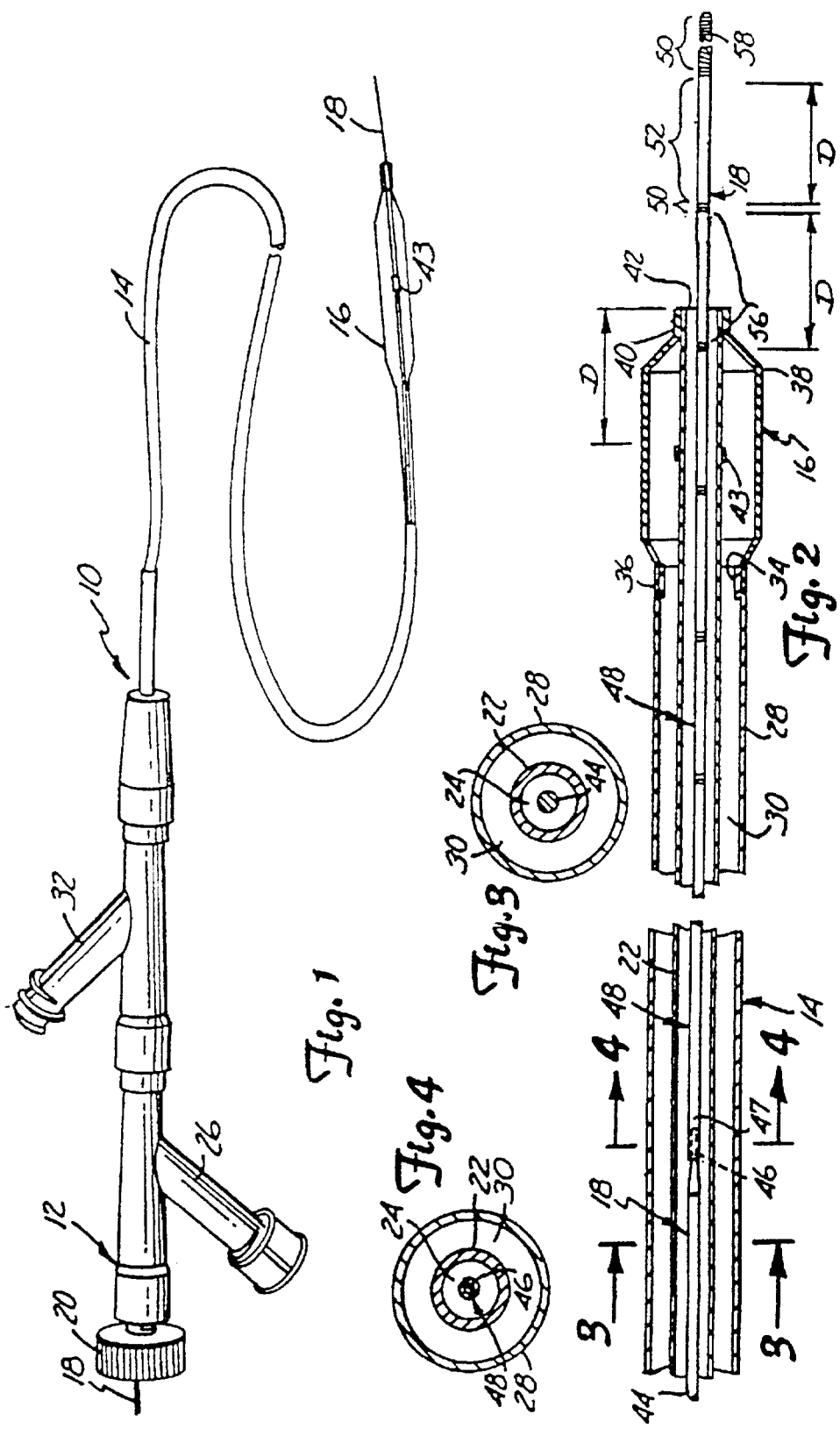

GUIDE WIRE WITH MULTIPLE RADIOPAQUE SECTIONS AND METHOD OF USE

This is a continuation of application Ser. No. 07/969,047, filed Oct. 30, 1992 which is a continuation of application Ser. No. 07/452,710, filed Dec. 19, 1989 and issued as Pat. No. 5,209,730 dated May 11, 1993.

BACKGROUND OF THE INVENTION

1. Field of the Invention

The present invention relates to the field of angioplasty and in particular, to new and improved catheters for performing balloon angioplasty procedures on blood vessels.

2. Description of the Prior Art

Angioplasty has gained wide acceptance in recent years as an efficient and effective method for treating vascular diseases. Angioplasty is widely used in the treatment of stenosis within the coronary arteries, although it has been used for the treatment of stenosis in other areas of the vascular system.

The most widely used method of angioplasty makes use of a dilatation catheter which has an inflatable balloon member at a distal end and an inner lumen for acceptance of a guide wire (or only called an "over-the-wire catheter"). The guide wire is typically about 175 cm in length, and is threaded through the vascular system by tracking radiopaque markers contained at a distal tip of the guide wire, which are monitored on an x-ray fluoroscope. Once the guide wire is positioned, the dilatation catheter is pushed along the guide wire until its balloon member is across the stenosis. The balloon member is subsequently inflated with liquid, exerting pressure radially and outwardly against the stenosis, causing the artery wall to stretch and re-establishing an acceptable blood flow through the artery.

An area of stenosis is normally transparent to x-ray fluoroscope viewing, but can be seen by a periodic injection of dye into the artery. This periodic injection allows a limited time fluoroscopic viewing of the restricted artery flow caused by the stenosis, allowing the guide wire to be positioned across the stenosis and into a distal artery, which provides support for the dilatation catheter. However, because dye injections cause surgical complications, physicians disfavor injecting additional dye into the artery in order to properly position the balloon member. On the other hand, physicians want to complete the operation as quickly as possible in order to minimize radiation exposure to the patient and staff. Thus, physicians do not want to spend a large amount of time trying to locate the stenosis. Therefore, there is a need for a method to properly mark a stenosis in order to timely position the balloon member without injecting additional dye.

In addition to properly positioning a first balloon member across the stenosis, some surgical procedures require the use of more than one dilatation catheter. For example, the balloon member of the first catheter might have a profile that is too large to fit into the stenosis. Using an extendable or exchange (300 cm in length) guide wire, a physician can exchange the first balloon member with a dilatation catheter having a second balloon member with a smaller profile, while attempting to maintain the guide wire in its position across the stenosis.

A dilatation catheter normally contains one or more markers to allow its balloon member to be located on a fluoroscope. To position the balloon member without the use of additional dye, a method must be used whereby the stenosis can be pinpointed while the stenosis is temporarily displayed. One method is to use a grease pen to mark the location of the stenosis on the screen of the fluoroscope. Another method is to take a picture of the fluoroscope screen while the stenosis can be seen and then use the picture to later position the balloon member across the stenosis.

As can be readily appreciated, these methods of positioning a balloon member are generally time consuming and relatively inaccurate. Also, they require the patient to remain perfectly still in order to have the location marked on the screen correspond to the actual location of the stenosis. Keeping the patient still is especially difficult when a second dilatation catheter is needed to perform the procedure because of the additional time required to complete the catheter exchange on the guide wire. Therefore, there is a need for an accurate method of positioning a balloon member of an over-the-wire dilatation catheter across a stenosis in a timely fashion and without injecting additional dye to locate the stenosis.

SUMMARY OF THE INVENTION

One embodiment of the present invention is a guide wire which has a radiopaque distal tip and three or more discrete highly radiopaque sections separated by relatively non-radiopaque sections on the distal portion. The highly radiopaque sections may be formed of coils and may have a width greater than their diameter. Similarly, the relatively non-radiopaque sections may have a width greater than their diameter- The radiopaque sections may be 1 mm in width and may be spaced 1.5 cm apart The distal tip of the guide wire may be a coil and the proximal portion may be a solid metal core.

In use, the guide wire is inserted into the vasculature of a patient and one of the radiopaque markers is positioned adjacent an anatomical feature inside the vasculature. The position of the radiopaque marker is maintained relative to the anatomical feature, thus marking the position of the feature. A catheter may be advanced over the guide wire and positioned such that the marker band of the catheter is adjacent one of the discrete radiopaque markers on the guide wire.

BRIEF DESCRIPTION OF THE DRAWINGS

FIG. 1 is a perspective view of an over-the-wire dilatation catheter system in accordance with the present invention.

FIG. 2 is an enlarged sectional view of a distal portion of a guide wire and an over-the-wire balloon dilatation catheter combination of the present invention.

FIG. 3 is a sectional view as taken on line 3—3 of FIG. 2.

FIG. 4 is a sectional view as taken on line 4—4 of FIG. 2.

DETAILED DESCRIPTION OF THE PREFERRED EMBODIMENTS

Catheter 10, as shown in FIGS. 1–4, is an over-the-wire balloon dilatation catheter which includes a manifold 12, a shaft 14, a balloon member 16 and a guide wire 18.

Manifold 12, defining a proximal portion of catheter 10, provides a means for introducing the guide wire 18 and inflation fluid for the balloon member 16 into the shaft 14. A thumb screw 20 is threadably mounted on a proximal end of manifold 12 for use in fixing the position of guide wire 18 relative to the manifold 12, shaft 14 and balloon member 16.

The shaft 14 has an inner tube 22 (see FIG. 2), which is preferably formed from a plastic material such as polyimide, and is attached to the manifold 12 to extend distally therefrom and define a guide wire lumen 24 for the guide wire 18. An inner surface of the inner tube 22 is coated with a lubricous material, such as polytetrafluoroethylene, to facilitate movement of the guide wire 18 therethrough.

The manifold 12 has a dye injection port 26 between the thumb screw 20 and the proximal end of the inner tube 22. The dye injection port 26 is in fluid communication with the guide wire lumen 24, and is adapted for connection to an inflation device (not shown) to provide fluid (e.g., radiopaque dye) under pressure to the guide wire lumen 24.

The shaft 14 also has an outer tube 28, attached to the manifold 12, which extends distally therefrom around the inner tube 22. An annular balloon inflation lumen 30 is thus defined between the outer tube 28 and the inner tube 22. The manifold 12 has a balloon inflation port 32 which is in fluid communication with the inflation lumen 30 and is adapted for connection to an inflation device (not shown) to provide fluid under pressure to the balloon member 16 via the inflation lumen 30.

The outer tube 28 is an elongated flexible elastic tube, preferably formed of polyimide. An outer surface of the outer tube 28 has a lubricous coating, such as polytetrafluoroethylene, which provides a slippery surface to aid in inserting and removing the catheter 10 into a guide catheter and into a patient's vascular system. At a distal end 34, outer tube 28 has a section of reduced diameter to which a proximal or waist segment 36 of balloon member 16 is attached, preferably by an adhesive seal such as epoxy.

Balloon member 16, which is preferably formed from a polymer material such as polyolefin, has the proximal or waist segment 36, a distensible balloon segment 38 and a small diameter distal segment 40. Distal segment 40 of the balloon member 16 is bounded to a distal end 42 of the inner tube 22, also preferably by an adhesive seal such as epoxy. A radiopaque balloon marker 43 is positioned about the inner tube 22 near a longitudinal center of the balloon member 16 at a distance D from a distal end of the catheter 10.

Guide wire 18 has a proximal solid wire portion 44 which is preferably formed of a high strength steel or other high strength alloy. The solid wire portion 44 has a tapered distal end 46 which is received within and bonded to a proximal end 47 of a coil spring member 48, preferably by a braze bond. Spring member 48 defines a distal portion of the guide wire 18, and is formed from a multiplicity of alternating groups of radiopaque 50 and non-radiopaque 52 spring coils of a high strength steel or other high strength alloy.

Radiopaque markers 56 for the guide wire 10 are formed by sandwiching one or more radiopaque spring coils 50 between nonradiopaque spring coils 52. A radiopaque tip 58 is formed at a distal end of spring member 48 by a plurality of radiopaque spring coils 50. Proximally from the tip 58, adjacent radiopaque markers 56 are longitudinally spaced by the same distance D as is between the distal end of the catheter 10 and its balloon marker 43. The width of the radiopaque markers 56 will depend upon the number of radiopaque spring coils 50 used to form each marker.

In a preferred embodiment, the spring member 48 is 25 cm in length. The distance D between the distal end of catheter 10 and the balloon marker 43 is 1.5 cm. Thus, the radiopaque markers 56 are also separated by 1.5 cm (distance D), with the radiopaque marker 56 closest to the radiopaque tip 58 being 1.5 cm from its proximal end. The width of each radiopaque marker 56 is preferably 1 mm. The total length of the guide wire is 175 cm.

The basic angioplasty procedure consists of inserting an introducer sheath, or short plastic tube, into a patient's thigh which provides an opening to the femoral artery. A guide catheter (not shown) is then advanced through the vascular system and into a position at the ostium of either the left or right coronary artery. The guide catheter is a hollow tube which serves as a channel from outside the patient's body through which catheter 10 can be advanced to the ostium of a coronary artery.

Prior to inserting the catheter 10 into the artery, the balloon member 16 is positioned on the guide wire 18 adjacent its distal radiopaque tip 58. Once in position, the thumbscrew 20 is tightened to fix the balloon member 16 position relative to the guide wire 18. The balloon member 16 and guide wire 18 assembly is then advanced to the ostium of the coronary artery. Using an inflation device which is connected to the dye injection port 26 or the guide catheter, a radiopaque dye is periodically injected into the artery to allow viewing of a stenosis on a fluoroscope. The thumbscrew 20 is loosened to allow the guide wire 18 to be advanced distally across the stenosis while it can be viewed on the fluoroscope. Of course, the guide wire 18 is also viewable on the fluoroscope. The balloon member 16 remains at the ostium of the coronary artery until the guide wire 18 is advanced to a point beyond the stenosis to provide stability to the catheter 10.

Once the guide wire 18 is properly advanced beyond the stenosis, a physician records the position of the stenosis relative to one of the radiopaque markers 56 on the guide wire 18. This recording provides a reference point for the stenosis and thus the periodic injection of dye (which had been necessary to locate the stenosis) can be ceased. The guide wire 18 i then held as still as possible across the stenosis while the balloon member 16 is advanced distally over the guide wire 18. This is done by manually grasping a proximal end of the guide wire 18 outside of the body. The balloon member 16 is advanced until its radiopaque marker 43 is aligned with the stenosis reference marker 56 of the guide wire 18. After the balloon member 16 is properly positioned with respect to the radiopaque marker 56, the thumbscrew 20 on the manifold 12 is tightened to prevent movement of the balloon member 16 relative to the guide wire 18.

The balloon member 16 is subsequently inflated via the inflation lumen 30 so that the distensible balloon segment 38 (shown inflated) expands, exerting pressure radially and outwardly against the stenosis and causing the artery wall to stretch. Once the dilation procedure is completed, the balloon member 16 is deflated and removed, re-establishing an acceptable blood flow through the artery.

The radiopaque markers 56 of the guide wire 18 allow the proper placement of balloon 16 across the stenosis without the need for additional continuous or even periodic injections of dye. This is advantageous to the patient because surgical complications arise from the dye injections. Also, this method allows the operation to be performed quickly and efficiently, thereby minimizing radiation exposure to the patient and staff.

The inventive method is also useful in angioplasty procedures which require the use of more than one balloon dilatation catheter. For instance, balloon member 16 of catheter 10 is sometimes too large to fit through the stenosis, or conversely, is so small that upon inflation of the balloon member 16, the stenosis is not sufficiently dilated. In these situations, balloon member 16 must be exchanged for a balloon member of a different size. If the balloon member 16 was too large to fit through the stenosis, a balloon member with a smaller profile must be used. On the other hand, if upon inflation of the balloon member 16 the stenosis was not sufficiently dilated, a balloon member with a larger inflated profile must be inserted to allow a widening of the dilated coronary artery.

In order to exchange balloon member 16 for a different balloon member, the guide wire 18 must be held outside the body (near the femoral artery) so that its position does not move relative to the stenosis. As the guide wire 18 is held in position, the thumbscrew 20 is loosened, allowing the balloon member 16 to be moved proximally along the guide wire 18 and out of the patient's body. The balloon member 16 is continually withdrawn until it is removed from the body and is completely removed from the proximal end of the guide wire 18.

A second dilatation catheter containing a correctly sized balloon member is then placed on the proximal end of the guide wire 18 and moved distally over the guide wire 18. The second dilatation catheter also has a radiopaque marker at a known point of its balloon member (preferably at its midpoint), and the second catheter is advanced along the guide wire 18 until the catheter's marker is aligned as desired with the recorded radiopaque marker 56 on the guide wire 18. The position of the balloon member of the second catheter is then fixed by again tightening the thumbscrew 22. During the entire exchange process, the physician attempts to hold the guide wire 18 steady and in place across the stenosis. If desired, dye may be injected to verify the position of the guide wire 18 and its recorded radiopaque marker 56 or the balloon member once it has been advanced to the recorded marker 56. The second balloon member is then inflated with an inflation medium, applying pressure radially and outwardly to the artery to dilate the stenosis and re-establish an acceptable blood flow through the artery. Upon completion of the angioplasty operation, the second dilatation catheter, guide wire 18, and guide catheter are removed from the patient's thigh.

By providing a guide wire with known spacings between radiopaque markers thereon, and a balloon dilatation catheter having a similar spacing known between its distal end and a radiopaque marker thereon, the positioning of the catheter balloon relative to the guide wire (which is positioned relative to the artery stenosis) is greatly facilitated. For example, if the fifth marker (from a distal end) on the guide wire is aligned across the narrowest point of the stenosis (as detected fluoroscopy), then the central marker of the balloon is moved over that fifth marker to place the balloon in the most advantageous position for inflation. As can be appreciated, once a marker on the guide wire is identified as across the stenosis, no further dye injections are necessary to align the catheter balloon, except to possibly recheck the guide wire marker location or to verify that balloon inflation has indeed dilated the artery.

The use of guide wire marker spacings equal to the distance from the distal end of the catheter to its balloon midpoint further assure the physician of balloon position and alignment by providing three reference points as to where the balloon member will be located when it is positioned across the stenosis. The three reference points are the fifth marker which will indicate the location of the midpoint of the balloon member, and the fourth and sixth markers on the guide wire which will indicate the location of the distal and proximal ends of the balloon member respectively. Thus, a physician can determine precisely how much of the stenosis will be contacted by the balloon member when it is inflated.

The balloon dilatation catheter assembly of the present invention thus has considerable advantages over those of the prior art. The invention places a plurality of radiopaque markers at a distal end of the guide wire, which in turn allows a method whereby a balloon member can be positioned properly relative to a stenosis. The radiopaque markers allow for efficient and timely placement of the balloon member without the need to constantly inject additional contrast dye. Consequently, the patient and staff are subject to less radiation exposure and the patient will have fewer complications from dye injections.

Although the present invention has been described with reference to preferred embodiments, workers skilled in the art will recognize that changes may be made in form and detail without departing from the spirit and scope of the invention.

What is claimed is:

1. A guide wire for use in combination with a catheter, the guide wire comprising an elongate shaft having a proximal portion, a distal portion and a distal tip, the distal tip being substantially more radiopaque than the proximal portion, the distal portion including three or more discrete highly radiopaque sections separated by relatively non-radiopaque sections.

2. A guide wire as in claim 1, wherein the highly radiopaque sections have a width and a diameter, the width being greater than the diameter.

3. A guide wire as in claim 1, wherein the relatively non-radiopaque sections have a width and a diameter, the width being greater than the diameter.

4. A guide wire as in claim 1, wherein the relatively non-radiopaque sections have a width greater than a width of the highly radiopaque sections.

5. A guide wire as in claim 1, wherein the distal tip comprises a coil.

6. A guide wire as in claim 5, wherein the proximal portion comprises a solid metal core.

7. A guide wire as in claim 1, wherein the radiopaque sections comprise coils.

8. A guide wire as in claim 1, wherein the distal portion includes four or more discrete highly radiopaque sections.

9. A guide wire as in claim 1, wherein the radiopaque sections are spaced 1–5 cm apart.

10. A guide wire as in claim 1, wherein the radiopaque sections are 1 mm in width.

11. A method of marking the position of an intravascular feature, the method comprising the steps of:

providing a guide wire having a distal portion and a plurality of discrete radiopaque markers disposed on the distal portion;

inserting the guide wire into the vasculature;

positioning one of the radiopaque markers adjacent to an anatomical feature inside the vasculature; and maintaining the position of the radiopaque marker relative to the anatomical feature.

12. A method as in claim 11, further comprising the steps of:

providing a catheter having a radiopaque marker band mounted on a distal end thereof;

advancing the catheter over the guide wire; and positioning the catheter such that the marker band of the catheter is adjacent one of the discrete radiopaque markers of the guide wire.

* * * * *

UNITED STATES PATENT AND TRADEMARK OFFICE
CERTIFICATE OF CORRECTION

PATENT NO. : 6,179,788 B1
DATED : January 30, 2001
INVENTOR(S) : Daniel J. Sullivan It is certified that error appears in the above-identified patent and that said Letters Patent is hereby corrected as shown below:

On the first page, under Abstract, first line, delete "lip" insert --tip--.

Column 6, claim 9, line 53, delete "1-5" insert --1.5--.

Signed and Sealed this

Fifteenth Day of May, 2001

Attest:

NICHOLAS P. GODICI

Attesting Officer     Acting Director of the United States Patent and Trademark Office